US006780361B1

(12) United States Patent
Sridharan et al.

(10) Patent No.: US 6,780,361 B1
(45) Date of Patent: Aug. 24, 2004

(54) PROCESS OF MAKING POLYMER ARTICLES

(75) Inventors: Srinivasan Sridharan, Morgan Hill, CA (US); Murthy V. Simhambhatla, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 37 days.

(21) Appl. No.: 10/174,073

(22) Filed: Jun. 17, 2002

Related U.S. Application Data

(63) Continuation-in-part of application No. 10/038,816, filed on Dec. 31, 2001.

(51) Int. Cl.[7] .......................... B29C 55/04; B29C 67/20; D01D 5/04; D01D 5/12; D01D 5/247

(52) U.S. Cl. ................. 264/205; 264/210.1; 264/210.5; 264/210.6; 264/210.8; 264/211.16; 264/211.19; 264/235; 264/235.6; 264/237; 264/291

(58) Field of Search .............................. 264/205, 210.6, 264/211.16, 211.19, 237, 210.1, 210.5, 210.8, 235, 235.6, 288.4, 288.8, 290.5, 291

(56) References Cited

U.S. PATENT DOCUMENTS

| | | | |
|---|---|---|---|
| 3,426,754 | A | 2/1969 | Bierenbaum et al. |
| 3,679,538 | A | 7/1972 | Druin et al. |
| 3,953,566 | A | 4/1976 | Gore |

(List continued on next page.)

FOREIGN PATENT DOCUMENTS

| | | |
|---|---|---|
| WO | WO 86/02656 A1 | 5/1986 |
| WO | WO 91/01210 A1 | 2/1991 |
| WO | WO01/45766 A1 | 6/2001 |

OTHER PUBLICATIONS

Hill, M.J., et al., *Direct Evidence for Distinctive, Stress–Induced Nucleus Crystals in the Crystallization of Oriented Polymer Melts*, Journal of Macromolecular Science, pp. 153–169, Mar. 1969.

Keller, A., *Unusual Orientation Phenomena in Polyethylene Interpreted in Terms of the Morphology*, Journal of Polymer Science, vol. XV, pp. 31–49, 1955.

Smook, Jan, et al., *Elastic Flow Instabilities and Shish–kebab Formation During Gel–Spinning of Ultra–High Molecular Weight Polyethylene*, Journal of Materials Science, vol. 19, pp. 31–43, 1984.

Sprague, B.S., *Relationship of Structure and Morphology to Properties of "Hard" Elastic Fibers and Films*, Journal of Macromolecular Science, vol. B6 (1–2), pp. 157–187, 1973.

van Hutten, P.F., et al., *Shish–Kebabs as an Intermediate Morphology in Gel–Spinning/Hot–Drawing of Polyethylene*, Polymer Communications, vol. 24, Aug. 1983.

(List continued on next page.)

*Primary Examiner*—Leo B. Tentoni
(74) *Attorney, Agent, or Firm*—Fulwider Patton Lee & Utecht, LLP

(57) ABSTRACT

A method including forming a pseudo-gel of a semi-crystalline polymer material and a solvent. The pseudo-gel is shaped into a first form and stretched. A portion of the solvent is removed to create a second form. The second form is stretched into a microstructure including nodes interconnected by fibrils. A method including forming a first form of a pseudo-gel including an ultra-high molecular weight polyethylene material and a solvent; stretching the first form; removing the solvent to form a second form; stretching the second form into a microstructure including nodes interconnected by fibrils; and annealing the stretched second form. An apparatus including a body portion formed of a dimension suitable for a medical device application and including a polyolefin polymer including a node and a fibril microstructure. An apparatus including a body portion including an ultra-high molecular weight polyolefin material including a node and a fibril microstructure.

25 Claims, 3 Drawing Sheets

U.S. PATENT DOCUMENTS

| | | | |
|---|---|---|---|
| 3,962,153 | A | 6/1976 | Gore |
| 4,187,390 | A | 2/1980 | Gore |
| 4,344,908 | A | 8/1982 | Smith et al. |
| 4,356,138 | A | 10/1982 | Kavesh et al. |
| 4,384,023 | A | 5/1983 | Okamura et al. |
| 4,413,101 | A | 11/1983 | Schmidt et al. |
| 4,536,536 | A | 8/1985 | Kavesh et al. |
| 4,655,769 | A | 4/1987 | Zachariades |
| 5,374,473 | A | 12/1994 | Knox et al. |
| 5,433,909 | A | 7/1995 | Martakos et al. |
| 5,643,511 | A | 7/1997 | Pluyter et al. |
| 6,120,477 | A | 9/2000 | Campbell et al. |
| 6,238,408 | B1 | 5/2001 | Kawabata et al. |
| 6,395,208 | B1 | 5/2002 | Herweck et al. |

OTHER PUBLICATIONS van Hutten, P.F. et al., *The Deformation Behaviour of Polyethylene Shish–Kebabs Produced by Stirring–Induced Crystallization*, Colloid and Polymer Science, vol. 262, No. 7, pp. 521–525, 1984.

van Hutten, P.F., et al., *The Plastic Deformation of Ultra–High Molecular Weight Polyethylene*, Journal of Materials Science, vol. 20, pp. 1556–1570, 1985.

Murthy, N.S., et al., *Structural Changes Prior to Melting in Extended–Chain Polyethylene Fibres*, Polymer Communications, vol. 31, pp. 50–52, Feb. 1990.

PROCESS OF MAKING POLYMER ARTICLES

CROSS-REFERENCE TO RELATED APPLICATION

The application is a Continuation-In-Part of co-pending application Ser. No. 10/038,816, filed Dec. 31, 2001 by applicants, Srinivasan Sridharan and Murthy V. Simhambhatla, entitled "Porous Polymer Articles and Methods of Making the Same".

BACKGROUND

1. Field

Polymer processing and more particularly to the formation of polymer products used in a variety of applications.

2. Background

Polymer constructs with a balance of porosity, strength, flexibility and chemical inertness or biocompatibility are desired in many biomedical and industrial applications.

In medical implant fields, polymers such as Dacron polyester and expanded polytetrafluoroethylene (ePFTE) have been used for medium and large diameter vascular prosthesis. Dacron prosthesis are generally woven or knitted into tubular constructs. The relatively large pore size resulting from knitting and weaving techniques allows blood to pass through these pores, necessitating either pre-clotting these constructs with the patient's blood before implantation, or impregnating the constructs with a biocompatible filler. The porosity of ePTFE can be tailored by adjusting the node and fibril structure, and consequently the porosity and pore size, such that blood is contained within the tubular structure under physiological conditions. Neither Dacron, nor ePTFE tubular constructs has however functioned effectively as small diameter vascular prostheses due to problems of thrombosis and anastomotic hyperplasia.

The flexibility, strength, biostability and ability to adjust porosity has also led to ePTFE being used for tissue augmentation in plastic surgery, in dura mater repair in neurosurgery, and for breathable, moisture-barrier cast liners. The combination of flexibility, lubricity and strength have also led to ePTFE use in dental floss.

In the medical device industry, angioplasty balloons are typically formed from thermoplastic nylons, polyesters, and segmented polyurethanes. To reduce the effective profile of the device for ease of delivery into the vasculature, balloons are folded on to the catheters. Upon inflation in the vasculature, the balloons unfold to assume a cylindrical profile. This unfolding generates non-uniform stresses in lesions during inflation. Furthermore, when stents are mounted on folded balloons, their deployment in the vasculature may be non-uniform due to the unfolding process. There is consequently a need for a balloon that is flexible, yet strong with the ability to be delivered in the vasculature in a small tubular profile without folding. Materials with node and fibril structures, that can be rendered auxetic, i.e., having a negative Poisson's ratio, with appropriate processing are particularly suitable for this application.

In the field of local drug delivery, there is a need for chemically inert and biocompatible microporous drug reservoirs for releasing drugs from transdermal patches. Polymers such as ultra-high molecular weight polyethylene (UHMWPE) may serve this need if they are rendered porous.

In the textile industry, ePTFE barrier layers are used for apparel that needs to be breathable, while preventing moisture from passing through the apparel.

UHMWPE is used as a separator membrane for electrochemical cells such as lithium-ion batteries, supercapacitors and fuel cells. For these applications, microporous UHMWPE membranes provide the right balance of porosity, wettability, flexibility and strength.

U.S. Pat. No. 5,643,511 discloses a process for the preparation of microporous UHMWPE by solvent evaporation from a gel-formed film. The films are stretched uniaxially or biaxially either during solvent evaporation or after solvent evaporation, to achieve the desired porosity. The microporous films thus obtained do not have a node and fibril structure.

U.S. Pat. No. 4,655,769 describes a process for preparing microporous UHMWPE by forming a pseudo-gel of UHMWPE sheet in a solvent, extracting the solvent with a more volatile solvent, evaporating the volatile solvent to create a semi-crystalline morphology and stretching the dry sheet. These films do not exhibit a well-defined node and fibril structure.

In regards to the above applications and limitations of current materials, there remains a desire for porous and flexible polymer constructs having high strength, good chemical inertness and biocompatibility, and which can preferably be made to exhibit auxetic behavior.

SUMMARY

A method is disclosed. The method includes, in one embodiment, forming a pseudo-gel of a semi-crystalline polymer material and a solvent. The pseudo-gel is shaped into a first form and stretched. A portion of the solvent is removed to create a second form, and the second form is stretched into a microstructure including nodes interconnected by fibrils. Such polymer article may be used in a variety of applications including, but not limited to, medical device applications such as in catheter balloons, and various grafts. Other applications include, but are not limited to, use in dental floss, sutures, filters, membranes, drug delivery patches, and clothing.

Ultra-high molecular weight polyethylene is one example of a suitable semi-crystalline polymer material. In another embodiment, a method including forming a first form of a pseudo-gel comprising an ultra-high molecular weight polyethylene material and a solvent at a temperature above a crystalline melting point of the ultra-high molecular weight polyethylene is disclosed. The first form is stretched and the solvent is removed to form a second form. The second form is stretched into a microstructure including nodes interconnected by fibrils.

An apparatus is also disclosed. In one embodiment, the apparatus includes a body portion formed of a dimension suitable for a medical device or other application. The body portion includes a polyolefin polymer material including a node and fibril microstructure formed by successive stretching of the polymer material in the presence of a solvent and in the absence of a solvent. In another embodiment, an apparatus including a body portion including an ultra-high molecular weight polyethylene material including a node and fibril microstructure is disclosed.

DETAILED DESCRIPTION

Figure 1:
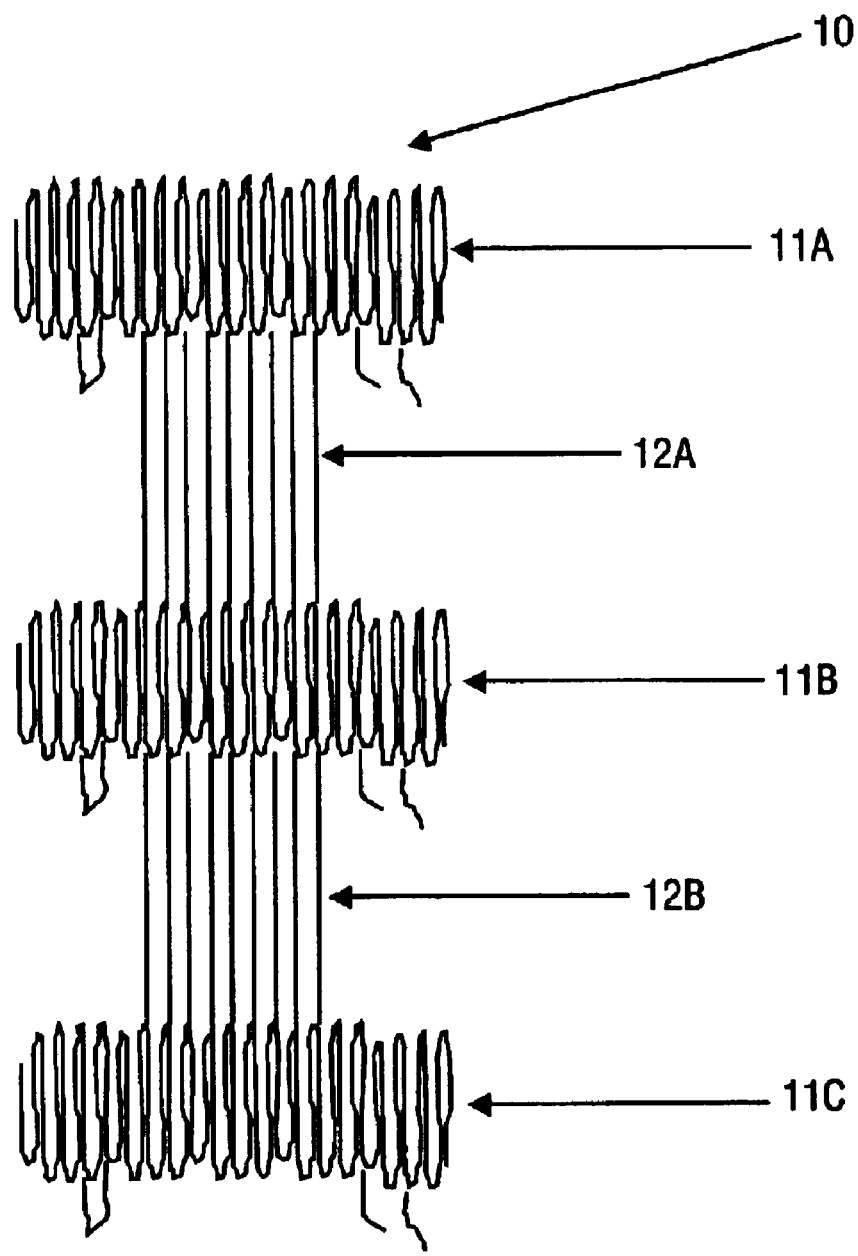
FIG. 1 shows a schematic side view of a polymer material including a node and fibril orientation.

FIG. 1 shows a polymer product formed according to the techniques described herein. The polymer product as shown in FIG. 1 is a portion of a polymer fiber having a "shish kebab" morphology formed from a semi-crystalline polymer crystallized from the melt state under high stress/strain fields. These polymers "row nucleate" with rows parallel to a draw direction (e.g., of an extruder) and a crystallite growth perpendicular to the direction of the draw. Highly anisotropic crystallites result.

FIG. 1 shows polymer structure 10 of node 11A, 11B, and 11C. Each node as described is formed from folded polymer chains. Between nodes in FIG. 1 are fibril portions 12A and 12B formed by, in one example, applying a tensile force to an extruded polymer (e.g., an extruded polymer fiber) in the direction of the draw. In effect, the tensile force pulls a portion of the polymer from a folded chain resulting in a folded portion (node 11A, 11B, 11C and a fiber-like portion (fibril portions 12A, 12B).

In one embodiment, polymer structure 10 is a semi-crystalline polymer material. Such semi-crystalline polymers include polyolefin polymers. Particular types of polyolefin polymers include polypropylenes and polyethylenes. Particular preferred polymers are high molecular weight or ultra-high molecular weight polyethylene (UHMWPE).

Suitable semi-crystalline polymers are those polymers that are generally not suitable for melt extrusion due to the viscosity of the polymer inhibiting the melt flow. Suitable polymers, such as polyethylene have molecular weights in the range of about 1 million grams per mole (gms/mole) to about 10 million gms/mole. This corresponds to a weight average chain length of $3.6 \times 10^4$ to $3.6 \times 10^5$ monomer units or $7 \times 10^4$ to $7 \times 10^5$ carbons. Polypropylene should have similar backbone carbon chain lengths. UHMWPE polymers are classified by molecular weight determination detailed in American Society for Testing Methods (ASTM) D1601 and D4020. Particularly, suitable polyethylene should have a molecular weight of at least about 500,000 gms/mole, preferably at least about 1,000,000 gms/mole, and more preferably at least about 2,000,000 gms/moleto about 10,000,000 gms/mole. Polymers that are commercially available in powder form that are suitable are GUR 4150™, GUR 4120™, GUR 2122™, GUR 2126™ manufactured by Ticona; Mipelon XM 220™ and Mipelon XM 221U™ manufactured by Mitsui; and 1900™, HB312CM™, HB320CM™ manufactured by Montell. Suitable polypropylenes have a molecular weight of at least 500,000 gms/mole, preferably at least about 1,000,000 gms/mole and more preferably at least about 2,000,000 gms/mole to about 10,000,000 gms/mole.

Figure 2:
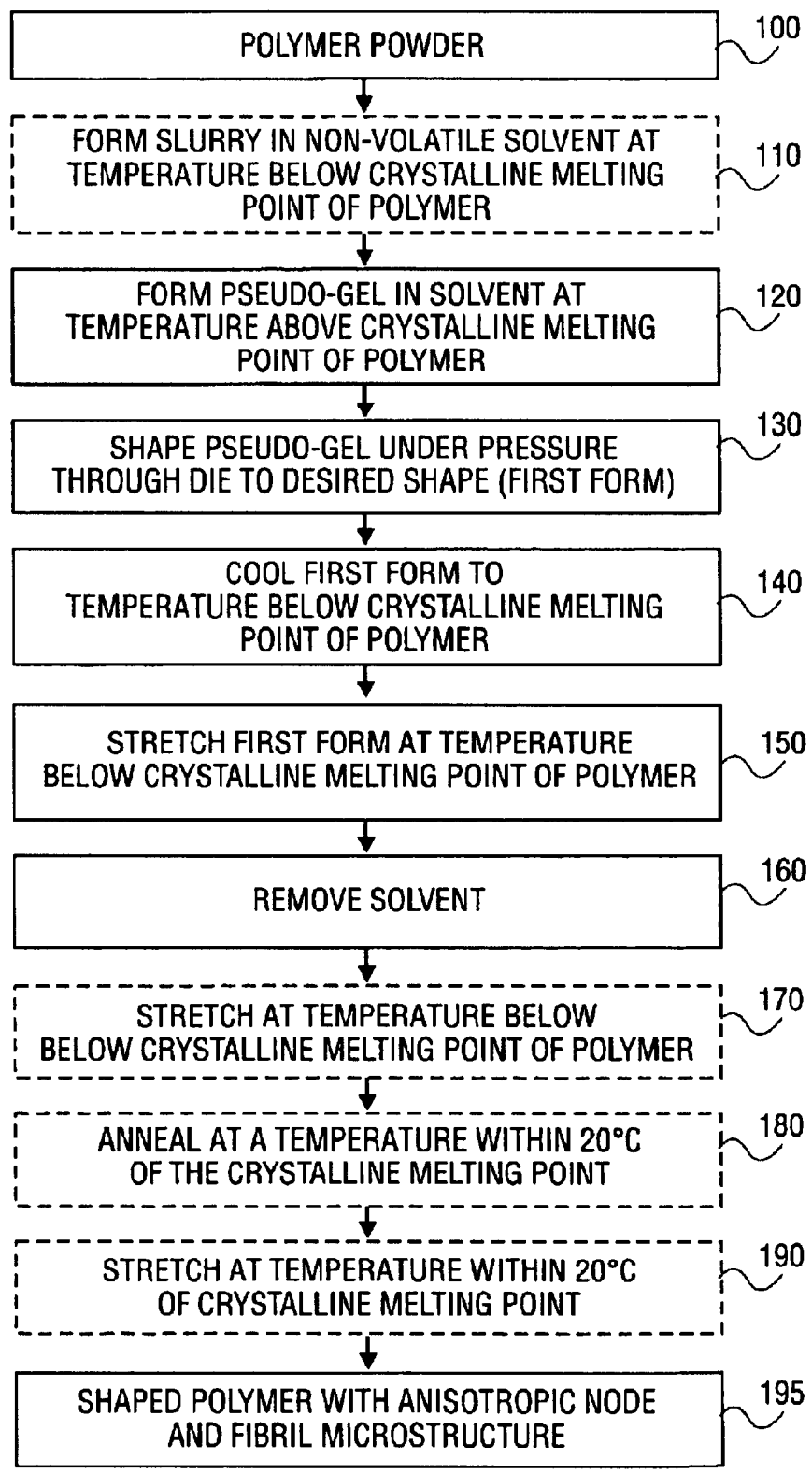
FIG. 2 is a flow chart of a process for making a polymer product.

FIG. 2 describes a process for forming a polymer product having a desired node and fibril microstructure. The polymer in this example is UHMWPE. In one embodiment as shown in FIG. 2, porous UHMWPE may be prepared from the starting UHMWPE powder (block 100) with optional processing aids. Optional processing aids include, but are not limited to, antioxidants (such as Irgonox) and slip agents. The UHMWPE (and optional processing aid(s)) is (are) combined with a solvent, such as a non-volatile solvent including, but not limited to, mineral oil or paraffin oil (such as Hydrobrite 550, Hydrobrite 380, Hydrobrite 1000 manufactured by Witco Corporation), and optionally formed into a slurry at a temperature below the crystalline melting point of the polymer (block 110). For UHMWPE, a suitable temperature is below about 140° C., and preferably below about 120° C. and more preferably below about 100° C., but above about 25° C. Alternatively, the UHMWPE (and optional processing aids(s)) may be combined with a volatile solvent such as decalin or p-xylene. The weight percent of the polymer in a slurry is in the range of about one weight percent (wt %) to about 50 wt % and preferably in the range of about 1 wt % to about 30 wt % and more preferably in the range of about 5 wt % to about 20 wt %.

The slurry of polymer powder and solvent (and optional processing aid(s)) is taken to a temperature above the crystalline melting point of the polymer to form a pseudo-gel (block 120). For UHMWPE, a suitable temperature is a temperature in the range of about 140° C. to about 325° C., preferably from about 180° C. to about 300° C. The pseudo-gel is formed using a mixing device, such as a stirred vessel or a single screw extruder or a twinscrew extruder or a pipe with static mixers or a ram extruder. A pseudo-gel in this context may be thought of as having gel-like properties, typically without (or with less of) the cross-linking behavior seen in true gels. The pseudo-gel (first form) is then pushed under pressure of about 50 pounds per square inch (psi) to about 10,000 psi through a die to a first form, such as a fiber, or film, or tape (block 130).

The shaped pseudo-gel (first form) is cooled using a cooling medium such as air or water to a temperature below the crystalline melting point of the polymer. For a UHMWPE pseudo-gel, the pseudo-gel is cooled to a temperature below about 140° C., and preferably below about 100° C., more preferably below about 30° C. and most preferably below about 20° C. (block 140). The reduced temperature tends to cause folded chain row-nucleated structures to form in the microstructure. The pseudo-gel is stretched at a temperature below the crystalline melting point of the polymer. For UHMWPE, the pseudo-gel is stretched, at a temperature below about 140° C., preferably below about 50° C. and more preferably below about 40° C. and even more preferably below about 30° C. (block 150). The stretch ratio is preferably from about 1.1:1 to about 20:1. The amount of stretching effects the porosity of the polymer article formed. Stretching tends to increase the porosity and the orientation of the crystals. In one embodiment, the stretching is done at the same time as the cooling. In such case, further stretching may optionally occur after the first form is cooled to a temperature below the crystalline melting point of the polymer.

Where a non-volatile solvent is combined with the polymer in forming the pseudo-gel, the non-volatile solvent may be removed following cooling and stretching with a volatile solvent such as chlorinated hydrocarbons, cholorofluorinated hydrocarbons and other hydrocarbons such as pentane, hexane, heptane, cyclohexane, methylene chloride, trichloroethylene, toluene, carbon tetrachloride, trichlorotrifluoroethylene, diethyl ether and dioxane. Preferred volatile solvents are those that have atmospheric boiling points below about 90° C., preferably below about 80° C. and more preferably below about 60° C. (block 160). Excess volatile solvent may be removed from the first form by evaporation. The optional stretching described above (after cooling (block 140) and stretching (block 150)) may be done after the extraction of the non-volatile solvent by a volatile solvent and the evaporation of the volatile solvent. Where a volatile solvent is combined with the polymer in forming the pseudo-gel, the volatile solvent may be flashed off as the first form exits the die. With the removal of the solvent (nonvolatile or volatile), a second form of the article results.

Following removal of the solvent, the second form may be optionally stretched at a temperature below the crystalline melting point of the polymer (block 170). A suitable stretch ratio is on the order of 1.1:1 to 10:1 to define a node and fibril microstructure.

Following removal of the solvent and optional stretching, the second form may be optionally annealed at, for example, a temperature within 20° C. of the melting point (block 180). For UHMWPE, a suitable temperature is, for example, on the order of about 130° C. to 160° C., preferably 130° C. to 150° C. Additionally, an optional hot stretching (block 180) such as on the order of 130° C. to 150° C. (stretch ratio on the order of 1.1:1 to 10:1) may be added to increase porosity or increase mechanical properties by increasing crystalline and amorphous orientation. It is believed that hot stretching will also result in a modification of the folded chain microstructure of the crystallites. The result is a shaped UHMWPE porous article (block 195). The porosity of the final article is preferably at least about 10% by volume and more preferably at least about 30% by volume.

The final product has a microstructure as determined by scanning electron microscopy (SEM) to consist of nodes of about one micron to about 100 microns in the largest dimension, which are connected together by means of thin, long polymer fibrils. The internodal distance (IND), which is the distance between the nodes varies from about 10 microns to about 500 microns. In one embodiment, the fibrils are oriented in all possible directions, leading to an isotropic structure. In another preferred embodiment, the nodes are about 10 microns to about 25 microns, and the IND is about 25 microns to about 125 microns. In another preferred embodiment, the nodes are about 10 microns to about 25 microns, and the IND is about 200 microns to about 500 microns. The node and fibril microstructure tends to make the polymer exhibit auxetic behavior (i.e., have a negative Poisson's ratio).

EXAMPLE

The following example describes the formation of UHMWPE tape with a node and fibril microstructure formed from a pseudo-gel of the polymer and a non-volatile solvent.

UHMWPE powder (XM 221U Mipelon commercially available from Mitsui, Japan) was mixed with mineral oil (Hydrobrite 550PO from Witco, a division of Crompton Corporation) to form a slurry that was 15 wt % polymer. The slurry was stirred continuously and heated to a temperature of 90° C. for 2 hours in a glass beaker. This gave enough time for the oil to diffuse into the particles of the polymer, causing some swelling of the particles.

A Rheotester 2000 (RT 2000) was fitted with a tape die, with exit notch dimensions of 5 mm wide and 0.025 inches thick. The die had a conical tapering inlet to enable smooth flow of the polymer. The taper angle was approximately 15°. The RT2000 and the die were pre-heated to a temperature of 290° C. The slurry was poured into the barrel to fill it up to the brim. A plunger rod was then placed so that it was in contact with the slurry. At that temperature, the slurry forms into a pseudo-gel as the temperature is above the melting point of UHMWPE (~143° C.). The pseudo-gel was maintained at that temperature for 10 minutes to give enough residence time for the gel to be uniform throughout the length of the barrel. The plunger rod was then pressed down into the barrel at a speed of 0.5 mm/sec. This causes the extrudate of the pseudo-gel to come out of the face of the die at a constant throughput. The tape extrudate was then quenched by immersing in a water bath (where the temperature of the water was about 20° C.). The distance between the face of the die and the level of the water bath was estimated to be about 2 to 3 inches. The cooled pseudo-gel tape was stretched by hand at a speed such that it did not break when coming out of the die.

The extraction of the mineral oil from the pseudo-gel was accomplished by extraction in a soxhlet apparatus for 16 hours with cyclohexane. The cyclohexane was then removed from the tape by evaporating in an oven for 16 hours at 50° C. Tapes were stretched by hand to stretch ratios of approximately 3:1 to 6:1. As the tape is stretched, smaller nodes and longer fibrils result.

In one embodiment the porous UHMWPE product formed as described above can be used for medical device application such as catheter balloons, stent grafts, Abdominal Aortic Aneurysm (AAA) grafts, vascular access grafts, pacemaker lead components, guiding catheter liners, Coronary Artery Bypass Grafts (CABG). Suitable applications include, but are not limited to, those described in commonly-assigned PCT/US00/34226 (Publication No. WO01/45766), titled *Medical Device Formed of Ultrahigh Molecular Weight Polyolefin*. In addition to these applications, porous UHMWPE can be used in dental floss, sutures, filters, permeable membranes, battery terminal separators, breathable fabrics, ballistic shields, packaging films, and drug delivery patches.

Figure 3:
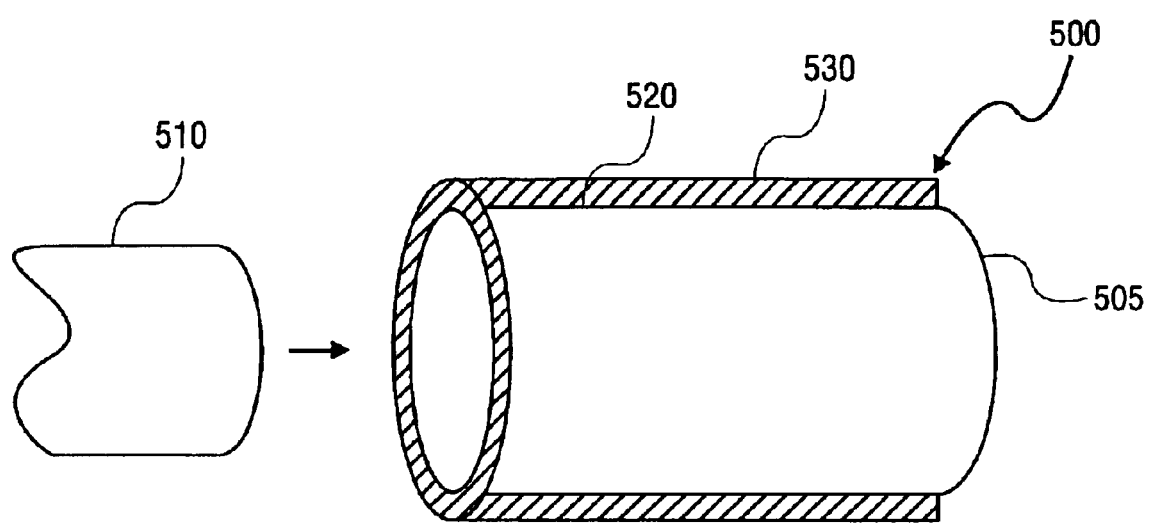
FIG. 3 is a schematic, perspective side view of a catheter incorporating a balloon.

FIG. 3 illustrates one representative article that is a catheter balloon assembly. Article 500 includes balloon portion 505 and catheter cannula 510. Balloon portion 505 may be coupled to an end of catheter cannula 510 by, for example, thermal or adhesive bonding.

Balloon portion 505 includes, in this embodiment inner tubular portion 520 and outer tubular portion 530. Inner tubular portion 520 is, for example, a non-porous polymer material having a thickness on the order of about 0.001 inches to 0.01 inches. Suitable polymers include, but are not limited to polyurethanes, polyisoprenes, and their copolymers. Overlying inner tubular portion 520 is outer tubular portion 530 of a semi-crystalline polymer such as UHMWPE formed as described above with reference to FIG. 2 and the accompanying text. In one embodiment, the semi-crystalline polymer is formed as a tape having a width on the order of 5 mm and a thickness on the order of 0.001 in. and wrapped on inner tubular portion 520. Outer tubular portion 530 is then fused to inner tubular portion 530 by heating the semicrystalline polymer to the melting point of the polymer. Alternatively the tape may be wrapped on a mandrel to and heated to its melting point to form a tubular balloon structure.

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. A method, comprising:

forming a pseudo-gel of a semi-crystalline polymer material and a solvent;

shaping the pseudo-gel into a first form;

stretching the first form;

removing a portion of the solvent to create a second form;

stretching the second form into a microstructure comprising nodes interconnected by fibrils;

annealing the second form having the node and fibril microstructure at an annealing temperature within 20° C. of a crystalline melting point of the polymer; and stretching the second form having the node and fibril microstructure at the annealing temperature.

2. The method of claim 1, wherein stretching the second form comprises stretching at a temperature below the crystalline melting point of the polymer material.

3. The method of claim 2, wherein stretching the second form comprises stretching at a temperature below 30° C.

4. The method of claim 1, wherein shaping comprises:
pushing the pseudo-gel through a shaping die to define the first form; and cooling the first form.

5. The method of claim 4, wherein the cooling and stretching of the first form are done simultaneously.

6. The method of claim 4, wherein the solvent is selected from the group consisting of mineral oil and paraffin oil.

7. The method of claim 6, wherein the solvent comprises a first solvent and removing a portion of the first solvent comprises contacting the first form with a second solvent.

8. The method of claim 7, further comprising removing a portion of the second solvent by evaporation.

9. The method of claim 1, wherein following stretching, annealing the article at a temperature sufficient to define the node and fibril microstructure.

10. The method of claim 1, wherein the polymer material comprises an ultra-high molecular weight polyolefin.

11. The method of claim 10, wherein the polyolefin comprises polyethylene.

12. The method of claim 1, wherein forming the pseudo-gel comprises including a processing aid with the polymer material and the solvent.

13. The method of claim 1, wherein prior to forming a pseudo-gel, the method comprises forming a slurry comprising the polymer and the solvent at a temperature below the crystalline melting point of the polymer.

14. A method, comprising:
forming a slurry comprising an ultra-high molecular weight polyethylene material and a solvent at a temperature below a crystalline melting point of the ultra-high molecular weight polyethylene material;
forming the slurry into a first form of a pseudo-gel comprising the ultra-high molecular weight polyethylene material and the solvent at a temperature above the crystalline melting point of the ultra-high molecular weight polyethylene material;
stretching the first form;
removing a portion of the solvent to form a second form;
stretching the second form into a microstructure comprising nodes interconnected by fibrils.

15. The method of claim 14, wherein stretching of the second form comprises stretching at a temperature below the crystalline melting point of the ultra-high molecular weight polyethylene material.

16. The method of claim 15, wherein stretching of the second form comprises stretching at a temperature below about 30° C.

17. The method of claim 16, further comprising:
shaping the first form; and
cooling the shaped first form.

18. The method of claim 17, wherein the cooling and stretching of the shaped first form are done simultaneously.

19. The method of claim 14, wherein the solvent is selected from the group consisting of mineral oil and paraffin oil.

20. The method of claim 14, wherein prior to forming the first form, the method comprises, combining the ultra-high molecular weight polyethylene material with the solvent, wherein the amount of the ultra-high molecular weight polyethylene material is on the order of 5 to 30 percent by weight.

21. The method of claim 4 further comprising, after stretching the second form, annealing the second form.

22. The method of claim 21, wherein the annealing comprises heating the second form at an annealing temperature within 20° C. of the crystalline melting point of the ultra-high molecular weight polyethylene material.

23. The method of claim 21, wherein after stretching and annealing the second form, the method comprises second stretching the second form at a temperature within about 20° C. of the crystalline melting point of the ultra-high molecular weight polyethylene material.

24. The method of claim 23, wherein after second stretching, the method further comprises annealing at a temperature within about 20° C. of the crystalline melting point of the ultra-high molecular weight polyethylene material.

25. A method, comprising:
forming a first form of a pseudo-gel comprising an ultra-high molecular weight polyethylene material and a solvent at a temperature above a crystalline melting point of the ultra-high molecular weight polyethylene material;
stretching the first form;
removing a portion of the solvent to form a second form;
stretching the second form into a microstructure comprising nodes interconnected by fibrils; and
annealing the second form having the node and fibril microstructure at a temperature within 20° C. of the crystalline melting point of the ultra-high molecular weight polyethylene material.

* * * * *

UNITED STATES PATENT AND TRADEMARK OFFICE
CERTIFICATE OF CORRECTION

PATENT NO. : 6,780,361 B1
DATED : August 24, 2004
INVENTOR(S) : Srinivasan Sridharan and Murthy V. Simhambhatla It is certified that error appears in the above-identified patent and that said Letters Patent is hereby corrected as shown below:

Column 6,
Line 19, delete "Deuice" and insert -- Device --.
Line 43, delete "semicrystalline" and insert -- semi-crystalline --.

Column 8,
Line 19, delete "claim 4" and insert -- claim 14, --.

Signed and Sealed this

Twelfth Day of April, 2005

JON W. DUDAS
*Director of the United States Patent and Trademark Office*